United States Patent [19]
Ellis et al.

[11] Patent Number: 5,752,932
[45] Date of Patent: May 19, 1998

[54] INTRAVASCULAR CATHETER WITH A RECOVERABLE GUIDE WIRE LUMEN AND METHOD OF USE

[75] Inventors: Louis Ellis, St. Anthony; David J. Blaeser, Champlin, both of Minn.

[73] Assignee: SciMed Life Systems, Inc., Maple Grove, Minn.

[21] Appl. No.: 436,781

[22] Filed: May 8, 1995

Related U.S. Application Data

[63] Continuation-in-part of Ser. No. 55,009, Apr. 29, 1993, abandoned.

[51] Int. Cl.[6] .................................................. A61M 29/00
[52] U.S. Cl. .............................. 604/96; 604/102; 606/194
[58] Field of Search .............................. 604/96–99, 102, 604/53, 280; 606/192, 194; 128/772

[56] References Cited

U.S. PATENT DOCUMENTS

| | | | |
|---|---|---|---|
| 3,834,394 | 9/1974 | Hunter et al. | |
| 4,295,464 | 10/1981 | Shihata | |
| 4,490,421 | 12/1984 | Levy | |
| 4,576,142 | 3/1986 | Schiff | |
| 4,601,713 | 7/1986 | Fuqua | 604/280 |
| 4,644,936 | 2/1987 | Schiff | |
| 4,697,573 | 10/1987 | Schiff | |
| 4,710,181 | 12/1987 | Fuqua | 604/280 |
| 4,738,666 | 4/1988 | Fuqua | 604/280 |
| 4,798,193 | 1/1989 | Giesy et al. | |
| 4,881,547 | 11/1989 | Danforth | |
| 4,909,252 | 3/1990 | Goldberger | 606/194 |
| 4,944,745 | 7/1990 | Sogard et al. | 606/194 |
| 4,958,634 | 9/1990 | Jang | 606/194 |
| 4,983,167 | 1/1991 | Sahota | 606/194 |
| 5,000,734 | 3/1991 | Boussignac et al. | 604/96 |
| 5,002,531 | 3/1991 | Bonzel | 604/96 |
| 5,019,042 | 5/1991 | Sahota | 604/101 |
| 5,049,131 | 9/1991 | Deuss | 604/96 |
| 5,078,685 | 1/1992 | Colliver | 604/96 |
| 5,085,662 | 2/1992 | Willard | 606/159 |
| 5,090,958 | 2/1992 | Sahota | 604/98 |
| 5,108,370 | 4/1992 | Walinsky | 604/96 |
| 5,147,377 | 9/1992 | Sahota | 604/194 |
| 5,160,321 | 11/1992 | Sahota | 604/96 |
| 5,180,367 | 1/1993 | Kontos et al. | 604/101 |
| 5,232,446 | 8/1993 | Arney | 604/96 |
| 5,267,958 | 12/1993 | Buchbinder et al. | 604/96 |
| 5,320,605 | 6/1994 | Sahota | 604/101 |
| 5,338,300 | 8/1994 | Cox | 604/96 |
| 5,368,567 | 11/1994 | Lee | 604/102 |
| 5,380,319 | 1/1995 | Saito et al. | 606/28 |
| 5,383,890 | 1/1995 | Miraki et al. | 606/194 |
| 5,395,332 | 3/1995 | Ressemann et al. | 604/96 |
| 5,409,458 | 4/1995 | Khairkhahan et al. | 604/96 |
| 5,520,647 | 5/1996 | Solar | 604/102 |
| 5,549,556 | 8/1996 | Ndondo-Lay et al. | 604/102 |

FOREIGN PATENT DOCUMENTS

| | | |
|---|---|---|
| 0611582A2 | 8/1994 | European Pat. Off. |
| WO 94/11048 | 5/1994 | WIPO |
| WO 94/11053 | 5/1994 | WIPO |

*Primary Examiner*—Michael Powell Buiz
*Assistant Examiner*—A. T. Nguyen
*Attorney, Agent, or Firm*—Nawrocki, Rooney & Sivertson, P.A.

[57] ABSTRACT

A catheter assembly including a guide wire having a proximal end, a distal end, and a balloon catheter. The balloon catheter includes a tubular member having a balloon proximate the distal end, and a guide wire tube having a lumen therethrough for slidably receiving the guide wire. The guide wire tube extends longitudinally along the exterior surface of the balloon from a point proximate the distal end of the balloon past the proximal end of the balloon. The guide wire tube is elastic and collapses radially when pressed against a vessel wall during inflation of the balloon. In a preferred method of use, the guide wire is placed in a first position across a treatment area followed by threading the balloon catheter over the guide wire so that balloon is also across the treatment area. The guide wire is then pulled in a proximal direction to a second retracted position, wherein the distal end of the guide wire is proximal of the proximal end of the balloon, yet within the guide wire tube. The balloon is then inflated for treatment followed by deflation. The guide wire is then pushed in the distal direction back to the first position, wherein the guide wire is across the treatment area.

22 Claims, 3 Drawing Sheets

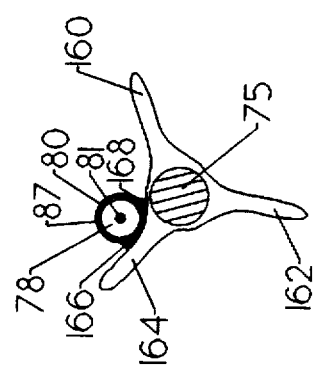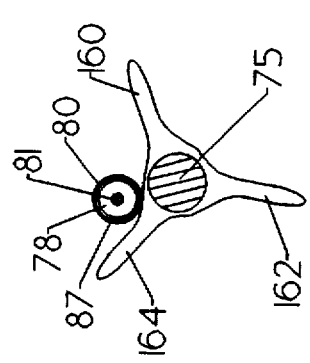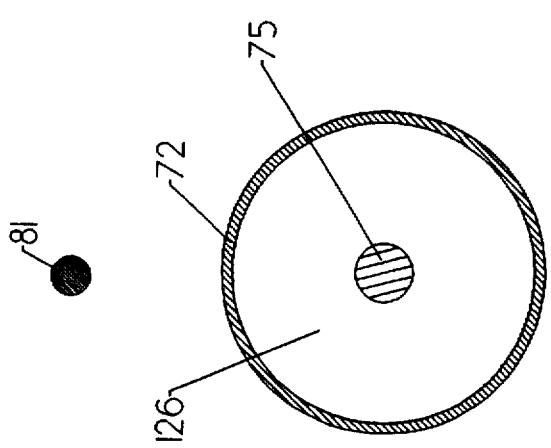

INTRAVASCULAR CATHETER WITH A RECOVERABLE GUIDE WIRE LUMEN AND METHOD OF USE

CROSS-REFERENCE TO CO-PENDING APPLICATIONS

This application is a continuation-in-part of U.S. patent application Ser. No. 08/055,009, now abandoned; filed Apr. 29, 1993, and entitled "DILATATION BALLOON FOR A SINGLE OPERATOR EXCHANGE INTRAVASCULAR CATHETER OR SIMILAR DEVICE", the disclosure of which is expressly incorporated herein by reference.

BACKGROUND OF THE INVENTION

The present invention relates to the field of angioplasty. In particular, the present invention relates to an intravascular catheter, such as a dilatation balloon catheter, of the type which is advanced over a guide wire and which has a guide wire lumen extending longitudinally over a portion of the length of the catheter adjacent the distal end of the catheter. This type of dilatation balloon catheter is generally referred to as a rapid exchange or single operator exchange catheter.

The placement of a dilatation balloon across a stenosis in a coronary artery can be a difficult procedure. Movement of the elongated dilatation balloon catheter (typically about 135 cm) is achieved by manual manipulation of its proximal end outside the patient. The ability of a catheter to bend and advance through the vasculature is commonly referred to as the "trackability" of the catheter. "Pushability" refers to the ability of the catheter to transmit the longitudinal forces applied by the physician along the catheter shaft to advance the distal end of the catheter through a coronary artery to and across the stenosis. Preferably, a catheter has a low profile, and is relatively trackable and pushable.

One common type of dilatation catheter has a separate guide wire lumen in the catheter so that a guide wire can be used to establish the path through the stenosis. The dilatation catheter can then be advanced over the guide wire until the balloon on the catheter is positioned within the stenosis. A recognized deficiency with this type of catheter is evident when it is desired to replace an existing catheter with another catheter. In that instance, the physician prefers to maintain the position of the guide wire in the patient's vascular system relative to the stenosis as the catheter is withdrawn over the guide wire. In the event of an abrupt closure of a partially dilated lesion when the balloon catheter has been withdrawn after an initial dilatation, the wire will maintain the path through the lesion. Any significant or uncontrolled movement of the exposed guide wire is avoided, so that the guide wire does not become dislodged from its position across the lesion.

In order to exchange a catheter with a guide wire lumen that extends the entire length of the catheter shaft, a longer exchange wire is sometimes exchanged for the standard guide wire, or a guide wire extension may be provided. The use of long exchange wires or guide wire extensions present a great length of guide wire outside the patient which must then be managed during the catheter exchange procedure. This not only proves awkward but typically requires two persons.

Rapid exchange catheter designs have overcome this problem. A first type of rapid exchange catheter includes a distal guide wire lumen which extends from a distal end of the catheter through the inside of the dilatation balloon and then exits the catheter at a point proximal of the balloon. This type of catheter is disclosed by Keith et al. in U.S. Pat. No. 5,217,482. With this design, catheter exchanges can be accomplished by a single operator with a guide wire which extends proximally outside of the patient's body only slightly more than the length of the distal guide wire lumen.

A rapid exchange catheter can be withdrawn without removing the guide wire from across the stenosis or utilizing a guide wire extension or extra long guide wire.

In utilizing a rapid exchange catheter, the guide wire is first grasped near the proximal end of the guide catheter. The catheter is then withdrawn until the proximal opening of the guide wire lumen is reached. The grasping hand is then moved incrementally away from the proximal opening of the guide wire lumen on the catheter. The catheter is then incrementally withdrawn until the catheter is fully removed from the guide catheter and the guide wire is thus again exposed and accessible adjacent to the proximal end of the guide catheter.

Once the initial catheter has been completely removed from the guide wire, a second catheter can be loaded onto the guide wire by inserting the proximal end of the guide wire into a distal opening of the guide wire lumen in the second catheter. This second catheter is then advanced by "feeding" the catheter distally over the guide wire while holding the guide wire stationary. The proximal end of the guide wire will then emerge out of the proximal opening of the distal guide wire lumen and is accessible again for gripping by the physician. By holding onto the exposed portion of the guide wire in this manner, the second catheter can then be advanced distally along the stationary guide wire to a desired position in the patient's vasculature.

A second type of rapid exchange catheter is constructed with the entire distal guide wire lumen adjacent the distal tip of the catheter (distally of the intravascular interoperative device (e.g., dilatation balloon) on the catheter). An apparatus having this configuration is described in U.S. Pat. No. 5,395,332, incorporated herein by reference. This structural design allows for a smaller catheter profile in the balloon area because a tube having a guide wire lumen extending therethrough does not have to be incorporated through the balloon. Further, the guide wire contacts the vessel wall during inflation of the balloon.

The short guide wire tube distal of the balloon does not, however, allow the guide wire to provide support for the catheter in the balloon area. Thus, without additional structure to provide rigidity along the catheter shaft and through the balloon, the pushability of the catheter can be reduced.

Buchbinder et al., in U.S. Pat. No. 5,267,958, disclose a rapid exchange balloon catheter having a body and one or more loops external to the body and spaced from the balloon for insertion of a guide wire. In one embodiment, Buchbinder et al. disclose a loop for the guide wire located proximally of the balloon, and a second loop located distally of the balloon with the guide wire extending through both of these loops. Buchbinder et al. assert that this design overcomes the deficiencies with the rapid exchange catheters that have a loop or ring which is located only distally of the balloon. Thus, the pushability and tracking of the device is asserted to be improved. Alternatively, Buchbinder et al. disclose a rapid exchange catheter wherein the guide wire fits through a sleeve which is located around the body of the catheter proximally of the balloon.

As depicted in FIG. 5 of Buchbinder et al., a first keeper is mounted on the catheter body proximal to the balloon, and a second keeper is mounted distally to the balloon. In use, Buchbinder et al. teaches that once the catheter is in place, the guide wire may be withdrawn from the second keeper to a position proximal of the balloon before the balloon is inflated. In this way, it is believed that the guide wire does not restrict the expansion of the balloon or become pressed into the stenosis upon inflation of the balloon. However, with the design of Buchbinder et al., once the guide wire has been retracted out of the second keeper which is distal of the balloon, it would be extremely difficult to reinsert the guide wire across the stenosis and through the second keeper or distal keeper. Thus, it may be difficult to return the guide wire to its position across the stenosis in order to perform a catheter exchange.

Kontos et al., in U.S. Pat. No. 5,180,367, disclose a procedure and apparatus for such procedure, whereby a small balloon catheter can be placed in a patient's body, expanded and collapsed as needed, and then a second larger balloon catheter placed over the smaller one. In FIG. 5, Kontos et al. depict an embodiment, wherein a sliding guide means begins at tip 58, terminates at 62, immediately adjacent the proximal end of chamber 36 (see, column 6, lines 45–50). In this embodiment, the sliding guide means 60 runs along the outside of the membrane 34. With this embodiment, it is clear that a guide wire could not be retracted to a point proximal of the balloon and reinserted due to the termination of the tube prior to the proximal end of the balloon. As such, it would be difficult to return the guide wire to its position across the stenosis in order to perform a catheter exchange.

SUMMARY OF THE INVENTION

The present invention is a rapid exchange type dilatation catheter, wherein a lumen for receiving the guide wire extends over only a portion of the length of the catheter proximate the distal end thereof. The means for slidably receiving the guide wire is mounted external to the catheter body and balloon, and preferably includes an elastic tubular member, which extends proximally from a point exterior to the catheter body distal of the inflatable balloon to a point exterior of the catheter body, proximal of the inflatable balloon.

In an exemplary embodiment of the present invention, the elastic guide wire tube is attached to the distal tip of the catheter assembly, extending alongside and externally to the dilatation balloon and catheter assembly, and finally is attached to the catheter body or tubular member proximally of the balloon. This combination does not require the guide wire tube to be fixedly attached to the balloon's outer surface.

The guide wire tube of the present invention is regularly collapsible and recoverable. That is, it is elastic, (i.e., it does not experience plastic deformation during inflation of the balloon) at least within the range of strains encountered when the tube is pinched between the balloon and the vessel wall. Thus, when the balloon is inflated, the guide wire tube contacts the wall and is sufficiently elastic so that the wall collapses radially and the guide wire tube flattens, closing the lumen therethrough. When the balloon is deflated, the guide wire tube recovers its original shape. It is recognized that lumen may remain partially deformed when the balloon is deflated. By recovery of its original shape, it is meant that the guide wire tube recovers sufficiently to allow the guide wire to pass therethrough.

This design allows the guide wire to easily be moved between a navigating or distal position and a retracted position for balloon inflation without the need to pry open the collapsed tube. The guide wire tube is also preferably non-self-adhering on its inner surface. It is recognized that some bio-compatible materials have a tendency to self-adhere when their surfaces are brought into contact with each other as when the lumen of the guide tube is collapsed during inflation. To allow the guide wire tube to return to its open position after being collapsed during balloon inflation, the inner surface is preferably non-self-adhering. This may be accomplished by the selection of proper materials or the addition of a coating (e.g. (silicone) on the inside surface of the guide tube.

In a preferred method of using the above-described catheter assembly, the guide wire is first placed in a first position across a treatment area. The balloon catheter is then threaded over the guide wire so that the guide wire extends through the guide wire tube, until the balloon is across the treatment area. The guide wire is then pulled in a proximal direction to a second, retracted position, wherein the distal end of the guide wire is proximal of the proximal end of the balloon, yet within the lumen of the guide wire tube. The balloon is then inflated and deflated as necessary to treat the restriction, while the guide wire is maintained in the second, retracted position. Upon completing treatment of the area, the balloon is deflated and the guide wire is pushed in a distal direction back to the first position, wherein the guide wire extends across the treatment area.

With this preferred method, the guide wire is not within the guide wire tube during the inflation and deflation of the balloon. This allows the guide wire tube to completely or more fully collapse as it is pressed against the vessel wall. Thus, the balloon in an inflated position retains a relatively circular cross section.

These and various other advantages and features of novelty which characterize the present invention are pointed out with particularity in the claims annexed hereto and forming a part hereof. However, for a better understanding of the invention, its advantages, and the object obtained by its use, reference should be made to the drawings which form a further part hereof, and to the accompanying descriptive matter in which there are illustrated and described preferred embodiments of the present invention.

It is recognized that the present invention may also work with catheter designs other than those embodiments described in the incorporated references.

BRIEF DESCRIPTION OF THE DRAWINGS

The invention will be further described with reference to the accompanying drawings where like numbers refer to like parts in several views and wherein:

FIG. 2 is a sectional view taken along line 2—2 in FIG. 1;

FIG. 3 is a sectional view of a first embodiment of the present invention taken along line 3—3 in FIG. 1 with the balloon in a deflated position;

FIG. 4 is a sectional view of a second embodiment of the present invention taken along line 3—3 in FIG. 1 with the balloon in a deflated position;

While the above identified drawing figures set forth several preferred embodiments, other embodiments of the present invention are also contemplated, as noted in the discussion. In all cases, this disclosure presents illustrative embodiments of the present invention by way of representation and not limitation. It should be understood that numerous other modifications and embodiments can be devised by those skilled in the art which fall within the scope and spirit of the principles of this invention. It should be noted that the figures have not been drawn to scale as it has been necessary to enlarge certain portions for clarity.

DETAILED DESCRIPTION OF THE PREFERRED EMBODIMENT

The present invention is a catheter assembly including a preferably elastic distal guide wire tube having a lumen extending therethrough. The guide wire tube may be affixed to the exterior of the catheter and/or balloon. The guide wire tube extends proximal of the distal tip over the exterior surface of the balloon. In an exemplary embodiment of the present invention, the elastic guide wire tube extends from the distal tip of the catheter assembly onto the outer surface of the dilatation balloon and is fixedly attached thereto. In another exemplary embodiment of the present invention, a distal end of the guide wire tube is attached to the distal tip of the catheter assembly and a proximal end of the guide wire tube is attached to a tubular member proximal of the balloon.

Figure 1:
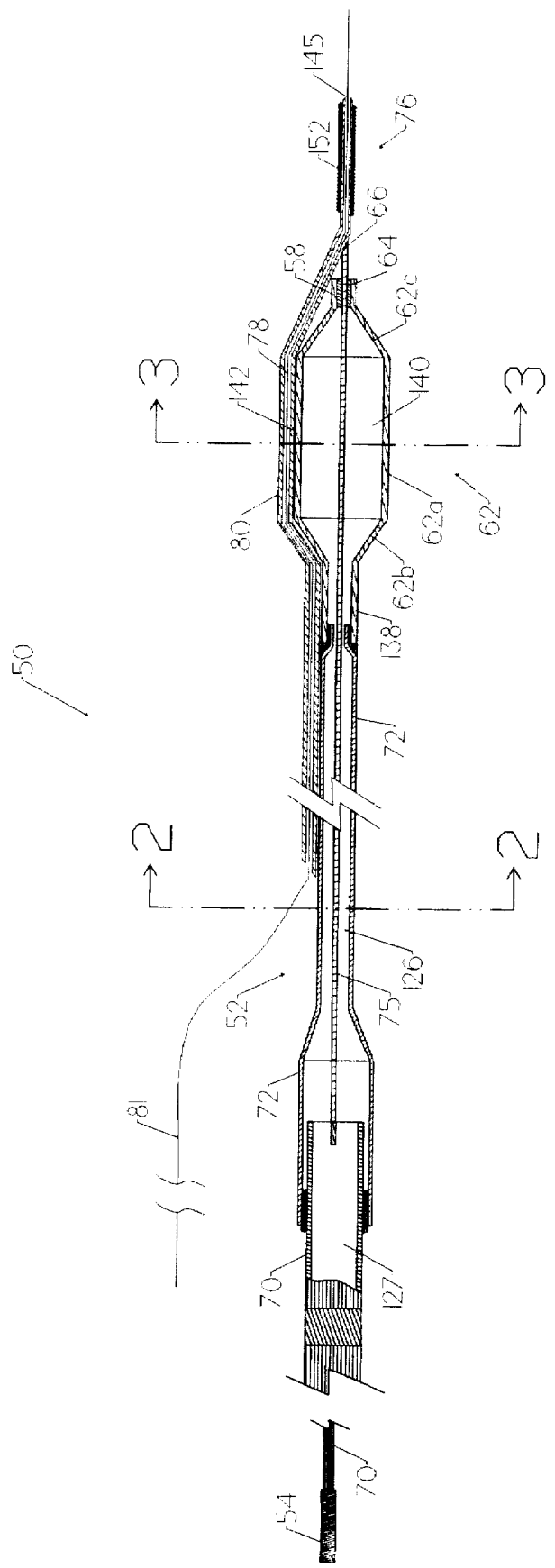
FIG. 1 is a cross-sectional view of an angioplasty balloon catheter incorporating a guide tube of the present invention.

FIG. 1 illustrates an exemplary embodiment of the present invention. In this embodiment, an angioplasty balloon catheter 50 has a shaft indicated generally as shaft 52 which has a mating member 54 of a luer connector on its proximal end and an inflatable balloon 62 on its distal end. Shaft 52 can include a first tubular segment 70 and a second tubular segment 72. The first tubular segment can include a metallic tube such as a stainless steel hypotube. With this configuration, the second tubular segment 72 is connected to a distal end of the first tubular segment 70 and extends distally therefrom. Balloon 62 (shown in an inflated position in FIG. 1) is connected proximate to a distal end of the second tubular segment 72 and extends distally therefrom. A core member 75 can extend longitudinally from the distal end of the first tubular segment 70 through the second tubular segment 72 and through the balloon 62 to a distal end thereof. Core member 75 is believed to improve the trackability and pushability of the catheter 50 as disclosed in U.S. application Ser. No. 07/922,902 incorporated herein by reference. The distal end of balloon 62 is preferably bonded to the core member 75 proximal of the distal end of the core member 75 at a point 64. A distal tip 76 may be connected to the core member 75 distally of the balloon 62, at a point 66.

In an exemplary embodiment, balloon 62 is attached to or proximate the distal end of the second tubular segment 72 and extends distally therefrom. Balloon 62 has an interior 140 which is in fluid communication with a lumen 126 of the second tubular segment 72 and a lumen 127 of the first tubular segment 70 thereby forming an inflation lumen extending the length of the catheter 50. A suitable balloon material is a polyolefin which has been treated by electron beam cross linking. Polyolefin is available from E. I. Du Pont de Nemours & Co. of Wilmington, Del. under the trade name SURLYN® (8527) Ionomer. However, it is recognized that other materials, such as polyethylene terephthalate (PET), polyether blocked amide (PEBA), or high density polyethylene (HDPE) may work as well. Balloon 62 may also be coated with a lubricous coating, such as a silicone lubricant.

The balloon length may vary depending upon the desired size of the dilatation catheter, but typically the lengths range from 10 to 50 mm. Furthermore, typical preferred inflated dilatation diameters for the balloon are 1.5 to 4 mm. In a preferred embodiment, the proximal waist 138 of the balloon is approximately 13 mm long, the expandable portion of the balloon (body 62a and cone portions 62b and 62c as seen in FIG. 1) is approximately 21–28 mm long depending on the desired balloon inflated diameter. Distal waist 58 of balloon 62 is approximately 1.5 to 3 mm long. In an alternative embodiment, the proximal waist 138 may extend proximally and connect to the first tubular segment 70.

Distal tip 76 may include a coil 152 having a proximal end and a distal end. The distal end of core member 75 may be connected to coil 152 adjacent its proximal end. A tubular liner (not shown) of lubricous polymeric material may be positioned within coil 152 to define a guide wire lumen 145 therethrough. However, it is recognized that the present invention is not limited to having a distal tip 76 with the guide wire lumen 145 therethrough. The distal portion of core member 75, coil 152 and the liner may all be encased by a plastic cover (not shown) to provide a smooth outer exterior for distal tip 76 and to facilitate bonding of those components together and to catheter 50.

In all embodiments of the catheter 50 of the present invention, means 80 for slidably receiving the guide wire 81 may be affixed to the outside surface of the catheter body 72, balloon 62, and/or distal tip 76 of catheter 50. In preferred embodiments, the means 80 for slidably receiving the guide wire 81 extend from a point distal of the balloon 62 proximal to a point proximal of the balloon 62. In one embodiment, the guide wire tube extends from a point distal of the balloon to a point at least 5 cm proximal of the balloon. The means 80 for slidably receiving the guide wire 81 is preferably a tubular element 80 which is elastic, wherein in use, the tube 80 collapses in a radial direction or flattens to essentially close the lumen therethrough in response to expansion of the balloon 62 and/or contact with the vessel wall so as not to restrict or prevent the balloon 62 from pressing into the stenosis being treated. As discussed below, the points of attachment for the means 80 for slidably receiving the guide wire 81 to the catheter body 72, balloon 62, and/or distal tip 76 can vary in preferred embodiments.

As depicted in FIG. 1, the means for slidably receiving the guide wire 81 is a guide wire tube 80, which is preferably elastic, having a guide wire lumen 78 extending therethrough. The expansion of the balloon 142 and resulting contact with the vessel wall causes the guide wire lumen 78 to be radially compressed between the outer surface of the balloon 62 and the vessel wall. Therefore, the guide wire lumen 78 decreases in size as the guide wire tube 80 is flattened radially.

In another exemplary embodiment, the guide wire tube 80 extends from a position proximal of the proximal end of the balloon 62 to the distal tip 76. It is contemplated that the guide wire tube 80 of the present embodiment can be attached to the distal tip 76 such that the guide wire lumen 78 of the guide wire tube 80 is aligned with the guide wire lumen 145 of the distal tip 76 thereby allowing a guide wire 81 to pass therethrough (see FIG. 1). However, it is contemplated that the distal end of the guide wire tube 80 may be positioned anywhere distal of the proximal end of the balloon 62 such that the guide wire tube 80 may be attached to a portion of the outer surface 142 of the balloon 62. It is further contemplated that the proximal end of the guide wire tube 80 may be positioned anywhere proximal of the proximal end of the balloon 62.

In another exemplary embodiment of the present invention, the guide wire tube 80 has a distal end and a proximal end wherein the distal end is attached to the proximal end of the distal tip 76, and the proximal end is attached to a portion of the second tubular member 72. When the balloon 62 is expanded by inflation, contact with the vessel wall causes the guide wire lumen 78 to be radially compressed against the outer surface 142 of the balloon 62.

In both of the above described embodiments, the guide wire tube 80 can provide a cushion between the guide wire and a blood vessel wall when pushed against such wall by the inflated balloon. Further, if the guide wire 81 is retracted to a point proximal of the balloon, prior to inflation, the elastic guide wire tube 80 does not interfere with expansion of the balloon, yet allows sliding the guide wire 81 distally across the stenosis when the balloon is deflated.

Guide wire tube 80 may be made from any polymeric material that is sufficiently elastic to collapse radially when pressed against a vessel wall. The term elastic is utilized herein to identify materials which do not experience plastic deformation when in use as a guide wire tube when the balloon is inflated. It is recognized that the guide wire tube need not collapse completely. Rather, it is preferred that the lumen 78 collapse enough to produce a generally smooth balloon surface profile when the balloon is inflated and the guide wire tube 80 is compressed against the vessel wall. More specifically, it is contemplated that guide wire tube 80 may be made from an elastomeric material, such as latex polyether block amide, polyurethane, polybutylene terephthalate/polyether block copolymer, neoprene, ethylene-propylene terapolymer, silicone rubber, polybutadiene, polyoxypropylene, and other suitable medical grade elastomers.

Figure 7:
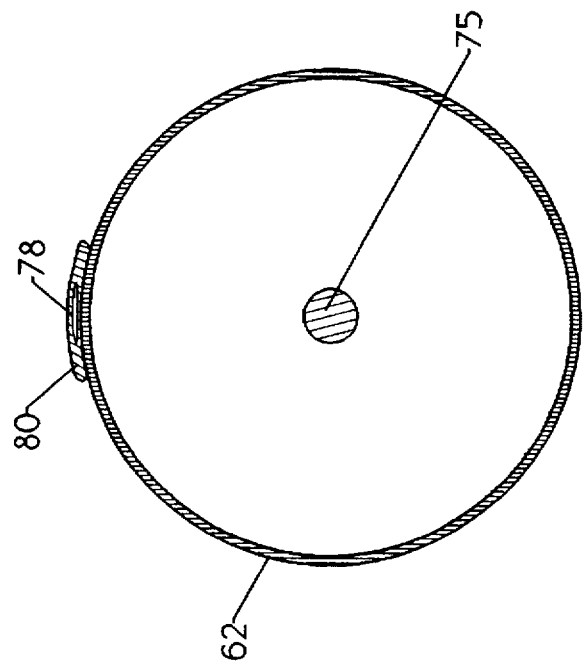
FIG. 7 is a sectional view of an embodiment of the present invention taken along line 3—3 in FIG. 1 with the balloon in an inflated position.

The tube 80 is preferably elastic to allow the tube to return to its navigating or open lumen position upon deflation of the balloon without pinching the wire. It is recognized that alternative materials may also be used to form the guide wire tube 80. When the elastic guide wire tube 80 is pressed against the vessel wall, the lumen therethrough collapses as depicted in FIG. 7. Materials must be selected for the guide wire tube 80 such that when the balloon is deflated, the lumen 78 of the guide wire tube 80 reappears and generally recovers its original open lumen so that the guide wire is slidably moveable therethrough. It is recognized that the lumen need only recover sufficiently for the guide wire to be reinserted therethrough. Thus, the material of construction of the guide wire tube 80 must be selected such that the inside walls of the tube do not stick to each other or self-adhere when collapsed. In the alternative, the inside of the guide wire tube 80 may be coated with a non-stick or non-self-adhering material 87 (see, Fig. 3 and 4), such as silicone to facilitate reforming of the guide wire tube lumen 80 when the balloon is deflated.

When using the present invention, it is envisioned that a guide wire 81 may be placed in a first position across a treatment area and then used to navigate the catheter 50 to the area of treatment, such as a stenosis. After the balloon 62 is placed across the stenosis, but before the balloon 62 is inflated, it is further envisioned that the guide wire 81 may be "pulled back" a sufficient distance to a second retracted position so that the guide wire 81 is no longer disposed in the portion of the guide wire lumen 78 that is adjacent to the balloon 62. This procedure may decrease the chance that the guide wire 81 will have an adverse effect on the dilated vessel by retaining a generally circular cross section when inflated. It is also contemplated that the guide wire may remain disposed in the guide wire lumen 78 while the balloon 62 is inflated, if desired.

FIG. 2 is a sectional view taken along line 2—2 in FIG. 1. This cross section illustrates that the core member 75 may be disposed substantially in the center of the second tubular segment 72.

FIG. 3 is a sectional view of a first embodiment of the present invention taken along line 3—3 in FIG. 1 with the balloon in a deflated position. The deflated balloon 62 may be constructed to form a plurality of wings. In this exemplary embodiment, the deflated balloon 62 includes wings 160, 162, and 164. In one embodiment of the present invention, the guide wire tube 80 can be attached to the wing 164 or as shown it is recognized that the guide wire tube 80 may be attached to any portion of the outer surface 142 of the balloon 62.

In another embodiment of the present invention, the guide wire tube 80 is not attached to the outer surface 142 of balloon 62, but rather the guide wire tube 80 is attached to the catheter assembly both proximal and distal of the balloon 62. For this embodiment, FIG. 3 shows the guide wire tube 80 placed adjacent to the outer surface 142 of the balloon 62, but not attached thereto.

FIG. 4 is a sectional view of a second embodiment of the present invention taken along line 3—3 in FIG. 1 with the balloon 62 in a deflated position. As stated above, the deflated balloon 62 may be constructed to form a plurality of wings. In an exemplary embodiment, the deflated balloon 62 includes a plurality of wings 160, 162, and 164. The guide wire tube 80 may be attached to a wing 164 or as shown it is recognized that the guide wire tube 80 may be attached to any other portion of the outer surface 142 of the balloon 62.

In the exemplary embodiment in FIG. 4, the guide wire tube 80 includes at least one attachment means 166, 168, such as a medical guide adhesive, a thermal bond, or an outer sleeve. It is contemplated that the attachment means 166, 168 may be any shape and may attach to the guide wire tube 80 at any predetermined position. It is further recognized that the attachment means 166, 168 may be physically part of the guide wire tube 80 or separate and distinct elements that are attached thereto.

Figure 5:
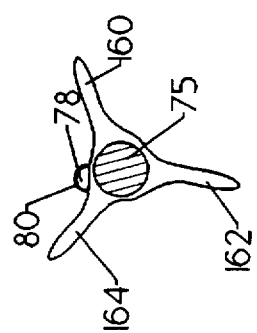
FIG. 5 is a sectional view of a third embodiment of the present invention taken along line 3—3 in FIG. 1 with the balloon in a deflated position.

FIG. 5 is a sectional view of a third embodiment of the present invention taken along line 3—3 in FIG. 1 with the balloon in a deflated position. As discussed above, the deflated balloon 62 may be constructed to form a plurality of wings. In the exemplary embodiment, the deflated balloon 62 includes a plurality of wings 160, 162, and 164. The guide wire tube 80 is attached to a wing 164 or as shown it is recognized that the guide wire tube 80 may be attached to any portion of the outer surface 142 of the balloon 62.

In the exemplary embodiment in FIG. 5, the guide wire tube 80 is not a "tube" but rather is dome shaped over at least a portion of its length and has a first end and a second end. The first end of the guide wire tube 80 is attached to the outer surface 142 of the wing 164 as shown. The second end is also attached to the outer surface 142 of the wing 164 at a predetermined distance from the first end of the guide wire tube 80 such that a sufficiently large guide wire lumen is formed between the guide wire tube 80 and the outer surface 142 of the balloon 62.

Figure 6:
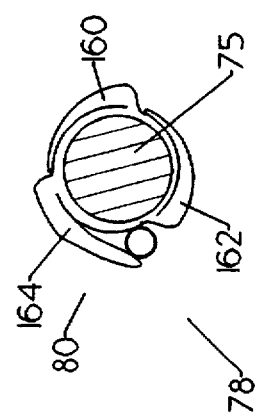
FIG. 6 is a sectional view of the first embodiment of the present invention taken along line 3—3 in FIG. 1 with the balloon deflated and wherein the deflated "wings" of the balloon are wrapped around the core member.

FIG. 6 is a sectional view of the second embodiment of the present invention taken along line 3—3 in FIG. 1 with the balloon in a deflated position, wherein the deflated "wings" of the balloon are wrapped around the core member 75. As stated above, the deflated balloon 62 may be constructed to form a plurality of wings. In an exemplary embodiment, the deflated balloon 62 includes a plurality of wings 160, 162, and 164 which are "wrapped" around the core member 75. The guide wire tube 80 is attached as shown, but it is recognized that the guide wire tube 80 may be attached to any point on the outer surface 142 of the deflated balloon 62. It is contemplated that the guide wire tube 80 may be placed in a predetermined portion of the outer surface 142 of the balloon 62 which minimizes the profile of the catheter 50.

In another embodiment of the present invention, the guide wire tube 80 is not attached to the outer surface 142 of the balloon 62, but rather the guide wire tube 80 is attached to the catheter assembly both proximally and distally of the balloon 62. For this embodiment, FIG. 6 shows the guide wire tube 80 placed adjacent to the outer surface 142 of the balloon 62, but not attached thereto. It is also recognized that the guide wire tube 80 can be attached both to the balloon and proximally of the balloon.

FIG. 7 is a sectional view taken along line 3—3 in FIG. 1 with the balloon in an inflated position. As can be seen from FIG. 7, the core member 75 is disposed substantially in the center of the balloon 62. The guide wire tube 80 also radially compresses, as depicted in FIG. 7, when it contacts the vessel wall.

An advantage of the present invention is that the guide wire lumen 78 may be used in conjunction with a guide wire during the insertion of the catheter device into a patient's vascular system, but during the inflation procedure, the guide wire may be pulled back so that the distal end of the guide wire is proximal of the balloon. The guide wire lumen 78 can then effectively disappear. Alternatively, if the guide wire remains disposed within guide wire lumen 78 while the balloon 62 is inflated, the guide wire tube 80 may provide an atraumatic contact between the guide wire and the vessel wall.

In a preferred method of utilizing the catheter and guide wire combination of the present invention, the guide wire and balloon catheter are first placed across the treatment area. It is recognized that the guide wire can first be placed in a first position across the treatment area. The balloon catheter can then be threaded over the guide wire, wherein the guide wire extends through the guide wire tube, until the balloon is across the treatment area. Alternatively, the guide wire and catheter can be inserted simultaneously. The guide wire is then pulled back in a proximal direction to a second, retracted position. The distal end of the guide wire is then proximal of the proximal end of the balloon, yet within the guide wire tube. The balloon is then inflated and deflated as necessary to treat the vascular restriction. Upon completing treatment, the balloon is deflated and the guide wire is pushed back in a distal direction to the first position, wherein the guide wire is across the treatment area. At this point, the catheter can be removed and yet retain the guide wire in a position across the stenosis or other vascular restriction to maintain a path for inserting a second catheter if necessary.

Although the present invention has been described with reference to preferred embodiments, workers skilled in the art will recognize that changes may be made in form and detail without departing from the spirit and scope of the invention.

What is claimed:

1. A balloon catheter device comprising:
   (a) an elongate shaft having a distal end and a proximal end;
   (b) an inflatable balloon attached to the distal end of the elongate shaft;
   (c) an elastic guide wire tube forming a guide wire lumen therethrough extending along an exterior of the balloon, wherein upon inflation of the balloon, the guide wire tube is radially compressed, substantially collapsing a portion of the guide wire lumen extending along the exterior of the balloon.

2. A balloon catheter as in claim 1, wherein the length of the guide wire tube is substantially less than the length of the elongate shaft.

3. A balloon catheter as in claim 1 wherein the guide wire tube extends from a point distal of the balloon to a point proximal of the balloon.

4. A balloon catheter as in claim 1, wherein the guide wire tube extends from a point distal of the balloon to a point at least 5 cm proximal of the balloon.

5. A balloon catheter as in claim 1, wherein the guide wire tube is sufficiently elastic to avoid permanent deformation after complete radial compression.

6. The catheter device according to claim 5, wherein the guide wire tube includes a non-self-adhering inside surface so that the lumen reappears when the balloon is deflated.

7. The catheter device according to claim 5, wherein the guide wire tube has an inside surface and the inside surface of the guide wire tube is coated with a non-self-adhering material.

8. A balloon catheter as in claim 1, wherein the guide wire tube is sufficiently elastic such that after the balloon is deflated, the guide wire tube substantially returns to its original decompressed geometry.

9. The catheter device according to claim 1, wherein the guide wire tube comprises a dome.

10. The catheter device according to claim 1, further comprising a distal tip, wherein a distal end of the guide wire tube is attached to a proximal end of the distal tip of the catheter device.

11. The catheter device according to claim 10, wherein the guide wire tube has a guide wire lumen and the distal tip includes a guide wire lumen extending therethrough, the guide wire lumen of the guide wire tube being aligned with the guide wire lumen of the distal tip such that a guide wire can extend therethrough.

12. A catheter device comprising:
   (a) an elongated shaft having a proximal end and a distal end;
   (b) a dilatation balloon having a proximal and a distal end disposed proximate the distal end of the shaft, the balloon having an inner and an outer surface; and
   (c) an elastic guide wire tube forming a guide wire lumen therethrough extending adjacent to a portion of the balloon along its exterior surface from a point proximate the distal end of the balloon to a point proximal of the proximal end of the balloon, wherein during use the guide wire tube contacts an inside wall of a body conduit, and radially compresses against the outer surface of the balloon, collapsing the guide wire lumen therethrough.

13. A catheter device as in claim 12, wherein the length of the guide wire tube is substantially less than the length of the elongate shaft.

14. A catheter device as in claim 12, wherein the guide wire tube extends from a point distal of the balloon to a point at least 5 cm proximal of the balloon.

15. A catheter device as in claim 12, wherein the guide wire tube is sufficiently elastic to avoid permanent deformation after complete radial compression.

16. The catheter device according to claim 15, wherein the guide wire tube includes a non-self-adhering inside surface so that the lumen reappears when the balloon is deflated.

17. The catheter device according to claim 15, wherein the guide wire tube has an inside surface and the inside surface of the guide wire tube is coated with a non-self-adhering material.

18. A catheter device as in claim 12, wherein the guide wire tube is sufficiently elastic such that after the guide wire tube is radially compressed against the balloon and the inside wall of the body conduit, the guide wire tube substantially returns to its original decompressed geometry.

19. A method for treating a vascular restriction comprising the steps of:
 (a) providing a catheter assembly including a guide wire having a proximal and a distal end, and a balloon catheter, said balloon catheter including a tubular member having a balloon proximate the distal end thereof and a guide wire tube having a lumen therethrough for slidably receiving said guide wire, wherein said guide wire tube extends longitudinally along the exterior surface of said balloon from a point proximate a distal end of said balloon past a proximal end of said balloon;
 (b) placing said guide wire and said balloon of said balloon catheter in a first position across a treatment area, wherein said guide wire extends through said guide wire tube;
 (c) pulling said guide wire in a proximal direction to a second retracted position;
 (d) inflating and deflating said balloon; and
 (e) pushing said guide wire in a distal direction to said first position across said treatment area.

20. The method of claim 19, wherein in said second retracted position, said distal end of said guide wire is proximal of the proximal end of said balloon within said guide wire tube.

21. A method for treating a vascular restriction comprising the steps of:
 (a) providing a catheter assembly including a guide wire having a proximal and a distal end, and a balloon catheter, said balloon catheter including a tubular member having a balloon proximate the distal end thereof and an elastic guide wire tube having a lumen therethrough for slidably receiving said guide wire, wherein said guide wire tube extends longitudinally along the exterior surface of said balloon from a point proximate a distal end of said balloon past a proximal end of said balloon;
 (b) placing said guide wire and said balloon of said balloon catheter in a first position across a treatment area, wherein said guide wire extends through said guide wire tube;
 (c) pulling said guide wire in a proximal direction to a second retracted position, wherein said distal end of said guide wire is proximal of the proximal end of said balloon within said guide wire tube;
 (d) inflating and deflating said balloon; and
 (e) pushing said guide wire in a distal direction to said first position across said treatment area.

22. A method for using a catheter device having a dilatation balloon proximate the distal end thereof, said balloon having a proximal and a distal end, and a guide wire tube disposed external to the dilatation balloon extending from proximate the distal end of the balloon past the proximal end of the balloon, comprising the steps of:
 (a) providing a guide wire and navigating the guide wire through the vascular system of a patient such that the guide wire is at a desired location relative to a treatment area;
 (b) threading the proximal end of the guide wire through the guide wire tube;
 (c) sliding the catheter device over the guide wire until the dilatation balloon is adjacent the treatment area;
 (d) pulling back the guide wire in a proximal direction a sufficient distance so that the guide wire is no longer disposed in the portion of the guide wire tube that is adjacent to the balloon;
 (e) inflating the balloon;
 (f) deflating the balloon after a predetermined period of time; and
 (g) pushing the guide wire in a distal direction through the guide wire tube across the treatment area.

\* \* \* \* \*